United States Patent
Youssef et al.

(10) Patent No.: US 9,649,263 B2
(45) Date of Patent: *May 16, 2017

(54) SUNSCREEN COMPOSITION CONTAINING HIGH LEVELS OF LIPOSOLUBLE UV FILTERS

(71) Applicant: L'OREAL, Paris (FR)

(72) Inventors: Sara Robyn Muenz Youssef, Middlesex, NJ (US); Catherine Chiou, Saddle Brook, NJ (US); Angelike A. Galdi, Westfield, NJ (US)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/744,903

(22) Filed: Jun. 19, 2015

(65) Prior Publication Data

US 2016/0367448 A1    Dec. 22, 2016

(51) Int. Cl.
| | | |
|---|---|---|
| *A61K 8/37* | (2006.01) | |
| *A61K 8/40* | (2006.01) | |
| *A61K 8/891* | (2006.01) | |
| *A61Q 17/04* | (2006.01) | |
| *A61K 8/06* | (2006.01) | |

(52) U.S. Cl.
CPC .............. *A61K 8/062* (2013.01); *A61K 8/37* (2013.01); *A61K 8/40* (2013.01); *A61K 8/891* (2013.01); *A61Q 17/04* (2013.01); *A61K 2800/30* (2013.01); *A61K 2800/591* (2013.01); *A61K 2800/805* (2013.01)

(58) Field of Classification Search
CPC .......... A61K 2800/30; A61K 2800/591; A61K 2800/805; A61K 38/4893; A61K 8/062; A61K 8/37; A61K 8/40; A61K 8/891; A61N 1/3605; A61N 1/36096; A61Q 17/04; C12Y 304/24069
See application file for complete search history.

(56) References Cited

U.S. PATENT DOCUMENTS

| | | |
|---|---|---|
| 5,599,533 A | 2/1997 | Stepniewski et al. |
| 6,548,074 B1 | 4/2003 | Mohammadi |
| 7,772,214 B2 | 8/2010 | Vatter et al. |
| 8,329,200 B2 | 12/2012 | Bauer et al. |
| 8,592,547 B2 | 11/2013 | Sakuta et al. |
| 2007/0274932 A1 | 11/2007 | Suginaka et al. |
| 2007/0297997 A1 | 12/2007 | Tanner |
| 2008/0038360 A1 | 2/2008 | Zukowski et al. |
| 2013/0230474 A1 | 9/2013 | Tanner |
| 2013/0345316 A1 | 12/2013 | Chiou |

FOREIGN PATENT DOCUMENTS

| | | |
|---|---|---|
| DE | 102008060656 A1 | 6/2010 |
| EP | 0813403 A1 | 12/1997 |
| EP | 1598045 A2 | 11/2005 |
| EP | 2334283 A2 | 6/2011 |
| JP | 11315009 A | 11/1999 |

OTHER PUBLICATIONS

Agache et al.(Measuring the Skin; 2004; Springer Science & Business Media: p. 29).*

* cited by examiner

*Primary Examiner* — Ernst V Arnold

(74) *Attorney, Agent, or Firm* — McNees Wallace & Nurick LLC

(57) ABSTRACT

A water-releasing sunscreen composition in the form of an emulsion and process for using the composition are provided. The composition includes an aqueous phase containing at least one water-soluble ingredient. The composition further includes an oil phase containing a first emulsifier and a liquid organic liposoluble UV filter. The liquid organic liposoluble UV filter is at a concentration from about 10% to about 25%. The composition includes a phase ratio of the aqueous phase to the oil phase of about 1.0 to about 12.0. The sunscreen composition is stable, has a sun protection factor (SPF) of greater than or equal to 15 and converts from an emulsion to a plurality of droplets upon application of shear.

20 Claims, No Drawings

SUNSCREEN COMPOSITION CONTAINING HIGH LEVELS OF LIPOSOLUBLE UV FILTERS

FIELD OF THE INVENTION

The present invention is directed to compositions containing liposoluble active ingredients and methods of using them. More specifically, the present invention is directed to a stable sunscreen composition in the form of water releasing emulsion containing high levels of liposoluble UV filters.

BACKGROUND OF THE INVENTION

Sunscreen compositions are applied to the skin to protect the skin from the sun's ultraviolet rays that can lead to erythema, a reddening of the skin also known as sunburn. Sunlight or ultraviolet radiation in the UV-B range has a wavelength of 290 nm to 320 nm and is known to be the primary cause of sunburn. Ultraviolet rays at a wavelength of 320 nm to 400 nm, known as UV-A radiation, produces tanning of the skin. However, in the process of doing so, the UV-A rays can damage or harm the skin.

The photoprotection of keratinous substrates, especially skin, is considered by many to be necessary in order to facilitate protection from sunburn and photo-aging, as well as to decrease the chances of skin cancer development. There are typically two types of UV sunscreens used to accomplish photoprotection, namely, inorganic UV filters and organic UV filters.

Inorganic UV filters, such as titanium dioxide and zinc oxide, are typically employed in large quantities in order to ensure proper coverage/maximum protection over the surface onto which they are applied. As a result, they have a tendency to feel dry and impart an undesirable white color onto the treated surface.

While it is desirable to utilize organic UV filters, the incorporation of liposoluble UV filters into emulsion-type compositions has posed various stability challenges. This has been especially true when the desire was to incorporate larger amounts of said ingredients into compositions. Examples of lack of stability include discoloration of the formula and/or precipitation of the ingredients out of the composition. The problem, however, is that such organic filters, due to their electrolytic properties, are difficult to formulate with when it comes to long-term stability. This lack of stability oftentimes manifests itself in the form of re-crystallization of the filters in the composition, causing them to separate from the emulsion. Liposoluble UV filters present a challenge for incorporation into emulsions intended for topical application onto a keratinous substrate, as most traditional emulsions are thickened and/or stabilized with natural or synthetic polymers, such as gums and polyacrylates, which are very sensitive to electrolytes.

It is therefore an object of the present invention to provide a composition capable of stably carrying liposoluble UV filters, which is also tactilely pleasing to consumers upon application.

BRIEF DESCRIPTION OF THE INVENTION

The present invention is directed to compositions containing liposoluble active ingredients and methods of using them. More specifically, the present invention is directed to a stable sunscreen composition in the form of water releasing emulsion containing high levels of liposoluble UV filters. The composition, according to the present disclosure, is capable of carrying high amounts of liposoluble ingredients in a texturally pleasing manner, without experiencing separation of the emulsion. The present invention also provides a water-releasing effect when applied onto a keratinous substrate such as skin, hair or nails. The water-releasing effect enables the composition, initially in the form of an emulsion, to be converted into a plurality of droplets upon application of shear, such as, for example, rubbing.

In an exemplary embodiment, a sunscreen composition in the form of a stable, tactilely pleasing emulsion containing significant amounts of at least one liposoluble active ingredient is provided. The composition includes an aqueous phase containing at least one water-soluble ingredient. The composition further includes an oil phase containing a first emulsifier and a liquid organic liposoluble UV filter. The liquid organic liposoluble UV filter is at a concentration from about 10% to about 25%. The composition includes a phase ratio of the aqueous phase to the oil phase of about 1.0 to about 10.0. The sunscreen composition is stable, has a sun protection factor (SPF) of greater than or equal to 15 and converts from an emulsion to a plurality of droplets upon application of shear.

In another exemplary embodiment, a method of inhibiting UV rays from contacting keratinous substrates is provided. The method includes applying the above-disclosed sunscreen composition, including liposoluble UV filters, onto the surface of a keratinous substrate, followed by application of force onto the composition present on the keratinous substrate.

Other features and advantages of the present invention will be apparent from the following more detailed description of the preferred embodiment which illustrates, by way of example, the principles of the invention.

DETAILED DESCRIPTION OF THE INVENTION

It has been surprisingly discovered by the inventors that high concentrations of liposoluble UV filters can be formulated into a stable water-in-oil type emulsion which, though initially in the form of a cream, possesses a transformative water-releasing effect upon application of force, such as, for example, shear.

One advantage of an embodiment of the present disclosure includes providing a stable composition or stable photoprotection composition capable of carrying relatively high levels of liposoluble ingredients without undergoing phase separation, i.e. re-crystallizing and/or breaking the emulsion. The water-releasing effect enables the composition, initially in the form of an emulsion, to be converted into a plurality of droplets carrying high levels of water-soluble ingredients upon application of force, such as, for example, shear, caused by an end user's rubbing of the composition onto the surface of a target keratinous substrate. The droplets, in turn, enable the water-soluble ingredients present in said droplets to effectively penetrate into a target keratinous substrate.

All numbers expressing quantities of ingredients and/or reaction conditions are understood as being modified in all instances by the term "about", unless otherwise stated.

"Keratinous substrate," as used herein, includes, but is not limited to, skin, hair, and nails.

"Force", as used herein, includes shear/friction produced by a rubbing motion of an end user's fingers, an electromechanical cleansing device having a movable brush with bristles, and/or an electromechanical device that produces a tapping motion, similar to one's fingers tapping on the surface of the skin.

"Homogenous" means substantially uniform throughout, i.e., a single phase mixture.

The term "liposoluble organic UV filter" means any organic compound for screening out UV radiation, which can be fully dissolved in molecular form or miscible in an oil phase or which can be dissolved in colloidal form (for example, in micellar form) in an oil fatty phase.

In the present application the term "ambient temperature" means a temperature of about 25° C.

In the present application, the term "stable" means the emulsion remains intact without phase separation, color and/or odor change over the stability monitoring period and the water-soluble active ingredients remain solubilized in the water phase and oil soluble active ingredients remain solubilized in the oil phase without crystallization or precipitation out of the emulsion.

In the present application, the term "water-releasing," as used herein, describes the phenomenon wherein, after application of a composition onto a target substrate, force is then applied onto the composition causing the water-in-oil type emulsion to rupture, which in turn causes the internal aqueous phase containing the water-soluble ingredient(s) to emerge in the form of droplets.

"Sun Protection Factor" or SPF is a value expressed mathematically by the ratio of the irradiation time necessary to attain the erythemogenic threshold with the UV screening agent to the time necessary to attain the erythemogenic threshold without UV screening agent. SPF generally provides information about the skin's resistance to ultraviolet B (UVB) radiation from the sun. The SPF rating system has been developed to provide consumer guidance in selecting sunscreens.

"Critical wavelength" is an absorption spectrum of a sunscreen composition characterized by an index, namely a wavelength, where the integral of the spectral absorbance curve reached 90% of the integral from 290 nm to 400 nm. The critical wavelength method is used to determine the breadth of UV protection.

The photoprotection composition and method of the present invention can comprise, consist of, or consist essentially of the essential elements and limitations of the invention described herein, as well as any additional or optional ingredients, components, or limitations described herein or otherwise useful in compositions intended for topical application onto keratinous substrates.

The water-in-oil emulsion system of the present invention typically has a white, glossy cream appearance. However, it may be modified so as to have a transparent gel-like or matte appearance by adjusting its refractive index. When the composition is deposited onto a target keratinous substrate, followed by application of force, the composition quickly releases the aqueous phase containing the water-soluble ingredients in the form of bead-like droplets, thereby enabling the water-soluble ingredients present in the aqueous phase to be forced into the surface of the target keratinous substrate. Likewise, when the photoprotection composition is deposited onto a target keratinous substrate, followed by application of force, the composition quickly releases the aqueous phase containing the water-soluble UV filters in the form of bead-like droplets, thereby enabling the water-soluble UV filters present in the aqueous phase to be spread onto the surface of the target keratinous substrate.

Aqueous Phase

In one embodiment, the aqueous phase present in the composition, according to the disclosure, includes at least one water-soluble ingredient, water, and other aqueous phase ingredients. The aqueous phase of the composition is at a concentration, by weight, of from about 60% to about 92%, or alternatively from about 65% to about 88%, or alternatively from about 70% to about 85% based upon weight of the composition.

In one embodiment, the aqueous phase present in the photoprotection composition, according to the disclosure, includes at least one water-soluble UV filter, water, and other aqueous phase ingredients. The aqueous phase of the photoprotection composition is at a concentration, by weight, of from about 60% to about 92%, or alternatively from about 65% to about 88%, or alternatively from about 70% to about 85%, based upon the weight of the photoprotection composition.

Water-Soluble Active Ingredient

In one embodiment, the aqueous phase present in the composition, according to the disclosure, includes at least one water-soluble active ingredient at a concentration, by weight, of from about 0.1% to about 20%, or alternatively from about 0.1% to about 15%, or alternatively from about 0.5% to about 10% based upon weight of the composition.

The water-soluble active ingredients can be present in their synthetic chemical compound forms, or alternatively as integral part of botanical extracts. Suitable examples of water-soluble ingredients, include, but are not limited to, (1) phenolic and polyphenolic compounds, and (2) other non-phenolic compounds.

The water-soluble active ingredients can be present in their synthetic chemical compound forms, or alternatively as integral part of botanical extracts. Suitable examples of water-soluble ingredients, include, but are not limited to, (1) phenolic and polyphenolic compounds, and (2) other non-phenolic compounds.

The salts of the compounds that may be used, according to the invention, are chosen in particular from salts of alkali metals, for example, sodium or potassium; salts of alkaline-earth metals, for example, calcium, magnesium or strontium; metal salts, for example, zinc, aluminum, manganese or copper, salts of ammonium of formula $NH_4+$; quaternary ammonium salts; salts of organic amines, for instance, salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts. Salts chosen from sodium, potassium, magnesium, strontium, copper, manganese or zinc salts are preferably used. The sodium salt is preferentially used.

Phenolic and polyphenolic compounds include, but are not limited to, flavones, chalcones, tannins, phenolic acids, catechins, anthocyanidins, stilbenoids, curcuminoids, phenylpropanenoids. Many of phenolic and polyphenolic compounds are well-known antioxidants and/or compounds that can provide skin care and cosmetic benefits. Particularly suitable compounds include baicalin, resveratrol, ferulic acid, ellagic acid, salicylic acid, and botanical extracts.

Other non-phenolic, water-soluble compounds include, but are not limited to, vitamins, xanthines, ceramides, cholesterols, sphingosines. C-glycosides, zwitterionic N-substituted amino sulfonic acid buffers, jasmonic acid and derivatives, hyaluronic acid and derivatives, sugars, nucleic acids, $\alpha$- and $\beta$-hydroxy acids, botanical extracts, aminopropyl triethoxysilane (APTES), dihydroxyacetone (DHA), amino acids, and peptides, and their derivatives and mixtures thereof.

Other non-phenolic, water-soluble compounds include, but are not limited to, vitamins, xanthines, ceramides, cholesterols, sphingosines, C-glycosides, zwitterionic N-substituted amino sulfonic acid buffers, sugars, nucleic acids, α- and β-hydroxy acids, botanical extracts, aminopropyl triethoxysilane (APTES), dihydroxyacetone (DHA), amino acids, and peptides, and their derivatives and mixtures thereof.

In one embodiment, in addition to and in combination with the liposoluble UV filters, water soluble UV filters are included in the composition, according to the present disclosure. In general, any water-soluble UV filters capable of absorbing UV light in the range of from about 280 to about 400 nm can be employed in the present invention.

Suitable examples of water-soluble UV filters that may be used include, but are not limited to, terephthalylidene dicamphor sulfonic acid (Ecamsule), phenylbenzimidazole sulfonic acid (Ensulizole), Benzophenone-4, Benzophenone-5, aminobenzoic acid (PABA), 4-Bis(polyethoxy)-para-aminobenzoic acid polyethoxyethyl ester (PEG-25 PABA), camphor benzalkonium methosulfate, methylene bis-benzotriazolyl tetramethylbutylphenol (Bisoctrizole), disodium phenyl dibenzimidazole tetrasulfonate (Bisdisulizole disodium), and tris-biphenyl triazine; their derivatives and corresponding salts; naphthalene bisimide derivatives, such as those described in European patent application EP1990372 A2, the entire contents of which is hereby incorporated by reference; and cinnamido amine cationic quaternary salts and derivatives, such as those described in U.S. Pat. No. 5,601,811, the entire contents of which is hereby incorporated by reference, and mixtures thereof.

Optional Hydrotropes

The composition of the present disclosure may optionally include hydrotropes. Examples of suitable hydrotropes include, but are not limited to, nicotinamide, caffeine, sodium PCA, sodium salicylate, urea, or hydroxyethyl urea. At least one or a combination of two or more hydrotropes can be used to improve the solubility of phenolic and polyphenolic compounds in the water phase.

Hydrotropes may be present in the compositions in amounts generally ranging from about 0.1% to about 20%, by weight, preferably from about 0.5% to about 10%, by weight, and most preferably from about 1% to about 5%, by weight, based on the total weight of the composition.

Stability Boosting Polyol

The aqueous phase present in the sunscreen composition, according to the disclosure, includes at least one stability boosting polyol at a concentration, by weight, of about 4% to about 35%, or alternatively about 5% to about 30%, or alternatively about 10% to about 25%, based upon weight of the composition.

"Stability boosting polyols", as utilized herein, include polyol compounds having at least one hydroxyl and are water-miscible, especially at room temperature (25° C.). Suitable stability boosting polyols include, but are not limited to, polyols containing from 3 to 20 carbon atoms, preferably containing from 3 to 10 carbon atoms and preferentially containing from 3 to 6 carbon atoms, such as glycerol (i.e., glycerin), propylene glycol, butylene glycol, pentylene glycol, hexylene glycol, dipropylene glycol or diethylene glycol, and the mixtures thereof.

Advantageously, the composition may comprise at least two water-miscible stability boosting polyols, especially a water-miscible polyol containing 3 carbon atoms and a water-miscible polyol containing more than 3 carbon atoms, especially containing from 4 to 20 carbon atoms, preferably containing from 4 to 10 carbon atoms and preferentially containing from 4 to 6 carbon atoms, and which may be chosen from the polyols mentioned above. According to one particular embodiment of the invention, the polyol containing 3 carbon atoms is present in predominant weight amount in the mixture of polyols present in the composition (which means that the weight content of polyol containing 3 carbon atoms is greater than the total content of water-miscible polyol containing more than 3 carbon atoms).

Water

The aqueous phase present in the composition or photoprotection composition, according to the disclosure, includes water at a concentration, by weight, of about 30% to about 92%, or alternatively about 35% to about 65% or alternatively about 40% to about 60%, based upon the total weight of the composition. The water used may be sterile demineralized water and/or a floral water, such as rose water, cornflower water, chamomile water or lime water, and/or a natural thermal or mineral water, such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say, a water comprising trace elements, such as zinc, copper, magnesium, etc., reconstituting the characteristics of a thermal water.

Oil Phase

The oil phase present in the composition or photoprotection composition, according to the disclosure, includes dimethicone, a first emulsifier, an optional second emulsifier, liposoluble UV filters, an optional structuring agent and an optional powder. The oil phase of the water-releasing composition is at a concentration, by weight, of about 8% to about 40%, or alternatively about 10% to about 35%, or alternatively about 20% to about 30%, based upon the total weight of the composition.

Dimethicone

The oil phase present in the composition or photoprotection composition, according to the disclosure, includes dimethicone at a concentration, by weight, of about 1% to about 25%, or alternatively about 2% to about 20%, or alternatively about 4% to about 15%, based upon weight of the composition.

First Emulsifier Gel

The first emulsifier is swelled in a volatile swelling agent or solvent. The resulting silicone elastomer-solvent mixture is in the form of a gel, herein hereafter as "first emulsifier gel". The amount of first emulsifier present in the silicone elastomer gel is preferably in the amount of about 10% to about 80%, by weight, more preferably in the amount of about 15% to about 60%, by weight, and most preferably in the amount of about 20% to about 40%, by weight, based on the total weight of the silicone elastomer gel.

The first emulsifier gel is preferably present in the composition, according to the invention, in an amount of from about 0.5% to about 40%, such as from about 1% to about 20%, preferably from about 5% to about 10%, by weight, based on the total weight of the composition.

Examples of suitable first emulsifier gels include emulsifying crosslinked siloxane elastomers swelled in a solvent, such as dimethicone, including, but not limited to, substituted or unsubstituted dimethicone/copolyol crosspolymer;

dimethicone and dimethicone/PEG-10/15 crosspolymers; substituted or unsubstituted dimethicone/polyglyceryl crosspolymer; dimethicone/polyglycerin-3 crosspolymer; dimethicone and PEG-15/lauryl polydimethylsiloxyethyl dimethicone crosspolymer, and combinations thereof. Such suitable emulsifying crosslinked siloxane elastomer gels are sold or made, for example, under the names of "KSG-210" a polyether-modified crosspolymer with an INCI name of dimethicone (and) dimethicone/PEG-10/15 crosspolymer, "KSG-710" a polyglycerin-modified crosspolymer with an INCI name of dimethicone (and) dimethicone/polyglycerin-3 crosspolymer, "KSG-380Z", a polyether-modified silicone cross-linked polymer, alkyl co-modified, with an INCI name of dimethicone (and) PEG-15/lauryl polydimethylsiloxyethyl dimethicone crosspolymer, "KSG-320Z", a polyether-modified silicone cross-linked polymer, with an INCI name of isododecane and PEG-15/lauryl polydimethylsiloxyethyl dimethicone crosspolymer, and "KSG-320", with an INCI name of isododecane (and) PEG-15/lauryl dimethicone crosspolymer, each available from Shin-Etsu Silicones of America, Inc. (Akron, Ohio).

First Emulsifier

The oil phase present in the sunscreen composition, according to the disclosure, includes a first emulsifier that is an emulsifying crosslinked siloxane elastomer at a concentration, by weight, of about 0.1% to about 20%, or alternatively about 0.3% to about 10%, or alternatively about 0.5% to about 7%, based upon weight of the composition.

The first emulsifier provides or enhances a water releasing effect within the composition. While not wishing to be bound by theory or explanation, it is believed that the first emulsifier entraps the water which is released upon application to the skin. The first emulsifier and the resultant properties significantly enhance the aesthetics of the formula architecture. In other embodiments, an optional further stabilizer, such as dimethicone/PEG-15/lauryl polydimethylsiloxyethyl dimethicone crosspolymer, may be utilized in addition, which further improves the aesthetics of the formula architecture.

Examples of suitable first emulsifiers include emulsifying crosslinked siloxane elastomers, including, but not limited to, substituted or unsubstituted dimethicone/copolyol crosspolymer; dimethicone/PEG-10/15 crosspolymers; substituted or unsubstituted dimethicone/polyglyceryl crosspolymer; dimethicone/polyglycerin-3 crosspolymer; PEG-15/lauryl polydimethylsiloxyethyl dimethicone crosspolymer, and combinations thereof. In one embodiment, the first emulsifier is dimethicone/PEG-10/15 crosspolymer. In another embodiment the first emulsifier is a combination of dimethicone/PEG-10/15 crosspolymer and PEG-15/lauryl polydimethylsiloxyethyl dimethicone crosspolymer.

Second Emulsifier

In one embodiment, the oil phase present in the composition, according to the disclosure, may optionally include a second emulsifier at a concentration by weight of about 0.01% to about 1.00%, or alternatively about 0.05% to about 0.90%, or alternatively about 0.07% to about 0.80%, based upon the total weight of the composition. If the second emulsifier concentration exceeds 1% by weight of the sunscreen composition, then the composition may still form an emulsion but the desirable transformative effect of cream changing to droplets upon application of shear is not achieved.

Suitable examples of second emulsifiers include polyether substituted linear or branched polysiloxane copolymers. One preferred second emulsifier is PEG-10 dimethicone available under the tradename of ES-5612 from Dow Corning Corporation (Midland, Mich.), or KF-6017 from Shin-Etsu (Akron, Ohio). Another preferred second emulsifier is dimethicone (and) PEG/PPG-18/18 dimethicone available under the tradename of ES-5226 DM from Dow Corning Corporation (Midland, Mich.). Other suitable second emulsifiers include, PEG-9 polydimethylsiloxyethyl dimethicone available under the tradename KF-6028 and PEG-9, lauryl PEG-9 polydimethylsiloxyethyl dimethicone available under the tradename KF-6038, both available from Shin-Etsu (Akron, Ohio). Another suitable example of a second emulsifier is polyoxyalkylene copolymers also known as silicone polyethers. Polyoxyalkylene copolymers are described in detail in U.S. Pat. No. 4,268,499, which is incorporated herein by reference in its entirety. A particularly preferred polyoxyalkylene copolymer is known by its CTFA designation as dimethicone copolyol. A particularly preferred form of dimethicone copolyol is supplied by Dow Corning as DC5225C.

Liposoluble UV Filters

The oil phase present in the sunscreen composition includes a UV filter having a liquid organic liposoluble UV filter. The oil phase present in the sunscreen composition, according to the disclosure, includes the liposoluble UV filter at a concentration, by weight, of greater than 10%, or alternatively about 10% to about 25%, or alternatively about 10% to about 20%, based upon weight of the composition.

In a preferred embodiment the liposoluble organic UV absorber (b) has water solubility of less than 1%, preferably less than 0.1% and most preferably of less than 0.01%, by weight, at room temperature and atmospheric pressure.

The present sunscreen composition, according to the present disclosure, includes a sun protection factor (SPF) of greater than or equal to 15 or SPF of at least about 15 to about 50 or SPF at least about 15 to about 30. In another embodiment, the composition optionally provides both 1) an SPF of greater than or equal to 15 or SPF of at least about 15 to about 50 or SPF at least about 15 to about 30, and 2) a critical wavelength of greater than 370 nm.

The liposoluble organic UV filters are in particular selected from cinnamate compounds, anthranilates, salicylate compounds, dibenzoylmethane compounds, camphor compounds, benzophenone compounds, 3,0-diphenylacrylate compounds, triazine compounds, p-aminobenzoate compounds (PABA), as described in the patent applications EP 0832642, EP 1027883, EP 1300137 and DE 10162844, UV-filter polymers and UV-filter silicones, as described in the patent application WO 93/04665, α-alkylstyrene dimers, as described in the patent application DE 19855649, 4,4-diarylbutadiens, as described in the patent applications EP 0967200, DE 19746654, DE 19755649, EP-A-1008586, EP 1133980 and EP 133981, merocyanine, as described in the U.S. Pat. No. 4,195,999, WO 2004/006878, WO 2008/090066, WO 2011113718, WO 2009027258, and the documents IP COM JOURNAL No. 000179675D published on Feb. 23, 2009, IP COM JOURNAL No. 000182396D published on Apr. 29, 2009, IP COM JOURNAL No. 000189542D published on Nov. 12, 2009, IP COM JOURNAL No. IP COM JOURNAL No. 000011179D published on Mar. 4, 2004 and their mixtures.

As examples, may be designed below under their INCI name:

Dibenzoylmethane Compounds:

Butylmethoxydibenzoylmethane sold especially under the tradename Parsol 1789® by DSM Nutritional Products, Inc.; Isopropyldibenzoylmethane.

Para-Aminobenzoic Compounds:
Ethyl PABA,
Ethyl Dihydroxypropyl PABA,
Ethylhexyl Dimethyl PABA sold under the name ESCALOL 507® by ISP,
Glyceryl PABA
Salicylic Derivatives:
Homosalate sold under the commercial name <<Eusolex HMS>> by Rona/EM Industries,
Ethylhexyl Salicylate sold under the commercial name <<NEO HELIOPAN OS>> by SYMRISE,
Cinnamic Derivatives:
Ethylhexyl Methoxycinnamate sold under the commercial name <<PARSOL MCX>> by DSM NUTRITIONAL PRODUCTS,
Isopropyl Methoxy cinnamate,
Isoamyl Methoxy cinnamate sold under the commercial name <<NEO HELIOPAN E 1000>> by SYMRISE,
Cinoxate,
Diisopropyl Methylcinnamate,
Derivatives of β,β-diphenylacrylate,
Octocrylene sold under the commercial name <<UVINUL N539>> by BASF,
Etocrylene sold under the commercial name <<UVINUL N35>> by BASF,
Benzophenone Derivatives:
Benzophenone-1 sold under the commercial name <<UVINUL 400>> by BASF,
Benzophenone-2 sold under the commercial name <<UVINUL D50>> by BASF,
Benzophenone-3 or Oxybenzone, sold under the commercial name <<UVINUL M40>> by BASF,
Benzophenone-6 sold under the commercial name <<Helisorb 11>> par Norquay,
Benzophenone-8 sold under the commercial name <<Spectra-Sorb UV-24>> by American Cyanamid,
Benzophenone-12,
n-hexyl 2-(4-N,N-diethylamino-2-hydroxybenzoyl)benzoate sold under the commercial name <<UVINUL A+>> or in the form of mixture with octylmethoxycinnamate under the commercial name <<UVINUL A+B>> by BASF,
Benzylidenecamphor Derivatives:
3-Benzylidene camphor manufactured under the commercial name <<MEXORYL SD>> by CHIMEX.
4-Methylbenzylidene camphor sold under the commercial name <<EUSOLEX 6300>> by MERCK,
Polyacrylamidomethyl Benzylidene Camphor manufactured under the commercial name <<MEXORYL SW>> par CHIMEX,
Phenyl Benzotriazole Derivatives:
Drometrizole Trisiloxane sold under the commercial name <<Silatrizole>> by RHODIA CHIMIE,
Triazine Derivatives
Bis-Ethylhexyloxyphenol Methoxyphenyl Triazine sold under the commercial name <<TINOSORB S>> by BASF,
Ethylhexyl triazone sold under the commercial name <<UVINUL T150>> par BASF,
Diethylhexyl Butamido Triazone sold under the commercial name <<UVASORB HEB>> by SIGMA 3V,
triazine silicones substituted by two aminobenzoates groups as those described in the patent EP 0841341, in particular 2,4-bis-(n-butyl 4'-aminobenzalmalonate)-6-[(3-{1,3,3,3-tetramethyl-1-[(trimethyl silyloxy] disiloxanyl}propyl)amino]-s-triazine.
Anthranilic Derivatives:
Menthyl anthranilate sold under the commercial name <<NEO HELIOPAN MA>> by SYMRISE,
Imidazoline Derivatives:
Ethylhexyl Dimethoxybenzylidene Dioxoimidazoline Propionate,
Benzmalonate Derivatives:
Di-neopentyl 4'-methoxybenzalmalonate,
Polyorganosiloxane with benzalmalonate functions as Polysilicone-15 sold under the commercial name <<PARSOL SLX>> by DSM NUTRITIONAL PRODUCTS
Derivatives of 4,4-Diarylbutadiene:
1,1-dicarboxy (2,2'-dimethyl-propyl)-4,4-diphenylbutadiene
Benzoxazole Derivatives:
2,4-bis-[5-1 (dimethylpropyl)benzoxazol-2-yl-(4-phenyl)-imino]-6-(2-ethylhexyl)-imino-1,3,5-triazine sold under the commercial name 'Uvasorb K2A>> by Sigma 3V
and mixtures thereof.
Lipophilic Merocyanine Derivatives
Octyl-5-N,N-diethylamino-2-phenylsulfonyl-2,4-pentadienoate
and mixtures thereof.
Particularly suitable liposoluble organic UV filters are selected from
Butyl Methoxy Dibenzoylmethane,
Ethylhexyl Methoxycinnamate,
Ethylhexyl Salicylate,
Homosalate,
Octocrylene,
Benzophenone-3,
n-hexyl 2-(4-N,N-diethylamino-2-hydroxybenzoyl)benzoate,
4-Methylbenzylidene camphor,
Bis-Ethylhexyloxyphenol Methoxyphenyl Triazine,
Ethylhexyl triazone,
Diethylhexyl Butamido Triazone,
2,4-bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
2,4-Bis(n-butyl 4'-aminobenzalmalonate)-6-[(3-{1,3,3,3-tetramethyl-1-[(trimethyl-silyl)oxy]disiloxanyl}propyl) amino]-s-triazine,
Drometrizole Trisiloxane,
Polysilicone-15,
1,1-Dicarboxy(2,2'-dimethylpropyl)-4,4-diphenylbutadiene,
2,4-Bis[4[5-(1,1-dimethylpropyl)benzoxazol-2-yl]phenylamino]-6-[(2-ethylhexyl)imino-1,3,5-triazine,
and mixtures thereof.
Particularly suitable liposoluble organic UV filters are more particularly selected from:
Octocrylene,
Ethylhexyl Salicylate,
n-Hexyl 2-(4-diethylamino-2-hydroxybenzoyl)-benzoate,
Bis-Ethylhexyloxyphenol Methoxyphenyl Triazine,
Ethylhexyl triazone,
Diethylhexyl Butamido Triazone,
Drometrizole Trisiloxane
And mixtures thereof.
In one embodiment, a solid organic liposoluble UV filter in combination with the liquid organic liposoluble UV filter may be included in the composition. Suitable solid organic UV filters include, but are not limited to, butyl methoxydibenzoylmethane, ethylhexyl triazone, drometrizole trisiloxane, benzophenone-3, diethylhexyl butamido triazone, bis-ethylhexyloxyphenol methoxyphenyl triazine, 4-methylbenzilidene camphor and/or benzoxazole. In one embodiment, the solid organic liposoluble UV filter is present in an amount of at least about 1% or at least about 2% or at least about 2.5% or from about 1.0% to about 5.0% or about 2.5% to about 3.5%, by weight of total composition.

Structuring Agent

The oil phase present in the sunscreen composition, according to the disclosure, includes at least one structuring agent at a concentration, by weight, of about 0.1% to about 5%, or alternatively about 0.5% to about 4%, or alternatively about 1% to about 3%, based upon weight of the composition.

Structuring agents, as utilized herein, include compounds, such as waxes, having the ability to simultaneously thicken and stabilize with an aesthetically pleasing feel, or a feel that does not diminish the cosmetic aesthetic, and does not disrupt the water releasing effect of the composition. The structuring agent results in selectively providing emulsion stability for the liposoluble UV filter within a water-in-oil emulsion.

Suitable examples of structuring agents that can be used, in accordance with the present disclosure, include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils, such as hydrogenated castor oil or jojoba oil; synthetic waxes, such as the polyethylene waxes, obtained from the polymerization or copolymerization of ethylene, and Fischer-Tropsch waxes, or else esters of fatty acids, such as octacosanyl stearate, glycerides which are concrete at 30° C., for example, at 45° C.

Other suitable examples of structuring agents in composition, according to the present disclosure, include at least one silicone wax. Examples of suitable silicone waxes include, but are not limited to, silicone waxes, such as alkyl- or alkoxydimethicones, having an alkyl or alkoxy chain ranging from 10 to 45 carbon atoms, poly(di)methylsiloxane esters which are solid at 30° C. and whose ester chain comprises at least 10 carbon atoms, di(1,1,1-trimethylolpropane) tetrastearate, which is sold or manufactured by Heterene under the name HEST 2T-4S; silicone resin waxes comprising at least 40 mole % of siloxy units having the formula $(R_2R'SiO_{1/2})_x(R''SiO_{3/2})$, where x and y have a value of 0.05 to 0.95, R is an alkyl group having from 1 to 8 carbon atoms, an aryl group, a carbinol group, or an amino group, R is a monovalent hydrocarbon having 9-40 carbon atoms, R" is a monovalent hydrocarbon group having 1 to 8 carbon atoms, an aryl group, such as those disclosed in US patent application 2007/0149703, the entire contents of which is hereby incorporated by reference, with a particular example being C30-C45 alkyldimethylsilyl polypropylsilsesquioxane; and mixtures thereof.

Optional Powders

The composition of the present disclosure may optionally include powders. The optional powders provide formulas that are smoother and softer on the skin. Representative powders include, but are not limited to, talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polystyrene powder, silk powder, crystalline cellulose, starch, titanated mica, iron oxide titanated mica, bismuth oxychloride, and the like. Additional powders include, but are not limited to, inorganic powders, such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder, such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder, such as hydroxyethyl cellulose and sodium carboxymethyl cellulose, ethylene glycol monostearate; inorganic white pigments, such as magnesium oxide. Representative cosmetic powders include, for example, polymethylsilsesquioxane, methyl polymethacrylate crosspolymer, Nylon-12, silica and boron nitride, the combinations thereof. Powders may be present in the compositions in amounts generally ranging from about 0.1% to about 5%, by weight, or about 0.1% to about 10% by weight, based on the total weight of the sunscreen composition.

Phase Ratio

The phase ratio is calculated by dividing the total weight of the aqueous phase by the total weight of the oil phase. The photoprotection composition of the present disclosure as a water-in-oil emulsion has a ratio, by weight, of the aqueous phase to oil phase of from about 1.0 to about 10.0, or alternatively about 1.0 to about 8.0, or alternatively about 1.0 to about 5.0, or alternatively about 1.0 to about 3.5. The phase ratio excludes any additional optional powders that may be added to the composition. Without intending to be bound by theory, this phase ratio is believed to be critical to: (1) the stability of the emulsion, and (2) the formation of droplets upon application of force onto the emulsion.

Water-Releasing Effect

With respect to the present invention, a good water-releasing effect of the water-in-oil emulsion means that the water-releasing effect results in a formation of plurality of water droplets upon the application on the back of the hand in a form of distinct spherical droplets or as a continuous streak of droplets. The water-releasing effect, as utilized herein, and in the below examples, is evaluated as pass/fail result in the evaluation method described below.

To determine whether the water releasing effect is present, about 0.2 g of a water-in-oil emulsion sample of the composition is taken and placed on the back of a hand, then it is applied thereon by circling gently with the middle finger and ring finger of the other hand, and then the phenomenon of the water-releasing effect is observed when the circling application reaches 20 cycles, and evaluated by pass/fail evaluation system. An evaluation result of "pass" indicates the formation of plurality of water droplets upon the application on the back of the hand in a form of distinct spherical droplets or as a continuous streak of droplets. An evaluation result of "fail" represents that no distinct water droplets or streak of water droplets appear.

In one embodiment, the water-releasing effect of the cosmetic composition of the present disclosure must have an evaluation result of "pass".

EXAMPLES

The method of making each of the examples provided in Tables 1-4 is generally the same. The examples in Table 4 include inventive examples of emulsions with incorporation of high concentrations of liposoluble UV filters having a water-releasing effect. The examples in Tables 1-3 are comparative examples illustrating the lack of emulsion stability and/or stabilization of active ingredients in a typical water-in-oil emulsion and/or lack a water releasing effect and/or fail to provide a sufficient SPF.

In each example (inventive and comparative), the viscosity of the emulsion is measured using a Rheomat with spindle #4 for 10 minutes.

The water-releasing effect of each example is measured by placing about 0.2 g of the cosmetic composition on the back of a hand, then applying thereon by circling gently with the middle finger and ring finger of the other hand. The phenomenon of the water-releasing effect is observed when the circling application reaches 20 cycles.

Microscopic images of the emulsion were captured to monitor the stabilization of the water-soluble ingredients in the emulsion. The Microscope is set at 10 time magnification, using a Leica DM2500 microscope and analyzed with the Leica Application Suite software.

All examples were monitored for emulsion stability and the stabilization of active ingredients for a period of 12 weeks at 25° C., 37° C. and 45° C. and after 10 cycles of freeze/thaw (ranged from −20° C. to 25° C.).

TABLE 1

Comparative Examples

| Phase | INCI US | Ex. 1 (Comparative) | Ex. 2 (Comparative) | Ex. 3 (Comparative) | Ex. 4 (Comparative) |
|---|---|---|---|---|---|
| A | DICAPRYLYL ETHER | 2.0 | 2.0 | 0 | 0 |
| A | DIMETHICONE | 6.0 | 5.0 | 5.0 | 5.0 |
| A | BUTYLOCTYL SALICYLATE | 0.0 | 0.0 | 0.0 | 2.0 |
| A | ETHYLHEXYL METHOXYCRYLENE | 0.0 | 0.0 | 2.0 | 0.0 |
| A | OCTOCRYLENE (1) | 5.0 | 5.000 | 5.0 | 5.0 |
| A | ETHYLHEXYL SALICYLATE (1) | 5.0 | 5.0 | 5.0 | 5.0 |
| A | ETHYLHEXYL TRIAZONE (2) | 3.0 | 3.0 | 3.0 | 3.0 |
| A | DIMETHICONE (and) DIMETHICONE/PEG-10/15 CROSSPOLYMER (3) | 6.0 | 7.00 | 7.0 | 7.0 |
| B | WATER, PRESERVATIVE | q.s | q.s | q.s. | q.s. |
| B | GLYCERIN | 15.0 | 15.0 | 15.0 | 15.0 |
| B | PROPANEDIOL | 3.0 | 3.0 | 3.0 | 3.0 |
| B | SODIUM HYDROXIDE | 0.025 | 0.025 | 0.025 | 0.025 |
| B | TEREPHTHALYLIDENE DICAMPHOR SULFONIC ACID (4) | 9.0 | 9.0 | 9.0 | 9.0 |
| B | TRIETHANOLAMINE | 1.8 | 1.8 | 1.8 | 1.8 |
| C | POLYMETHYLSILSESQUIOXANE | 0.5 | 0.5 | 0.5 | 0.5 |
| | TOTAL %: | 100.0 | 100.00 | 100.00 | 100.00 |
| | FIRST EMULSIFIER %: | 1.50 | 1.75 | 1.75 | 1.75 |
| | TOTAL WATER PHASE %: | 72.50 | 72.50 | 72.50 | 72.50 |
| | TOTAL OIL PHASE %: | 27.00 | 27.00 | 27.00 | 27.00 |
| | RATIO (WATER PHASE/OIL PHASE): | 2.69 | 2.69 | 2.69 | 2.69 |
| | INITIAL ASPECT: | White Cream | White Cream | White Cream | White Cream |
| | 24 HR VISCOSITY (MOBILE 4, 10 min): | 16.30 | 20.20 | 25.30 | 24.00 |
| | WATER RELEASING EFFECT: | Pass | Pass | Pass | Pass |
| | STABILITY RESULTS: | *failed stability at 1 week at 45 C. due to crystallization | *failed stability at 1.5 weeks at 45 C. due to crystallization | *failed stability at 4 weeks at 45 C. due to crystallization & liquid separation | *failed stability at 2 weeks at 45 C. due to crystallization |

(1) ORGANIC LIQUID LIPOSOLUBLE UV FILTER
(2) ORGANIC SOLID OIL SOLUBLE UV FILTER
(3) FIRST EMULSIFIER
(4) WATER SOLUBLE UV FILTER

TABLE 2

Comparative Examples

| Phase | INCI US | Ex. 5 (Comparative) | Ex. 6 (Comparative) |
|---|---|---|---|
| A | HOMOSALATE (1) | 4.0 | 4.0 |
| A | OCTOCRYLENE (1) | 1.25 | 1.25 |
| A | ETHYLHEXYL SALICYLATE (1) | 0.0 | 2.0 |
| A | BUTYL METHOXYDIBENZOYLMETHANE (2) | 2.0 | 2.0 |

TABLE 2-continued

Comparative Examples

| Phase | INCI US | Ex. 5 (Comparative) | Ex. 6 (Comparative) |
|---|---|---|---|
| A | ISODODECANE (AND) PEG-15/LAURYL DIMETHICONE CROSSPOLYMER (3) | 2.5 | 2.5 |
| A | TRIETHYLHEXANOIN (AND) VINYL DIMETHICONE/LAURYL DIMETHICONE CROSSPOLYMER | 0.0 | 4.0 |
| A | CETYL PEG/PPG-10/1 DIMETHICONE | 1.0 | 0.5 |
| A | DEXTRIN PALMITATE (4) | 0.3 | 0.0 |
| A | ISOPROPYL LAURYL SARCOSINATE | 2.0 | 2.0 |
| A | ISONONYL ISONONANOATE | 4.0 | 4.0 |
| A | ISOPROPYL ISOSTEARATE | 4.0 | 2.0 |
| A | ETHYLPARABEN | 0.1 | 0.1 |
| A | PROPYLPARABEN | 0.1 | 0.1 |
| B1 | WATER | 10.0 | 0.0 |
| B1 | TRIETHANOLAMINE | 0.55 | 0.0 |
| B1 | PHENYLBENZIMIDAZOLE SULFONIC ACID (6) | 1.00 | 0.0 |
| B2 | WATER | 51.0 | 57.35 |
| B2 | NIACINAMIDE | 4.0 | 4.0 |
| B2 | SODIUM CITRATE | 0.2 | 0.2 |
| B2 | SODIUM CHLORIDE | 0.5 | 0.5 |
| B2 | BENZYL ALCOHOL | 0.4 | 0.4 |
| B2 | DISODIUM EDTA | 0.1 | 0.1 |
| B2 | GLYCERIN (5) | 2.0 | 7.0 |
| B2 | PENTYLENE GLYCOL (5) | 3.0 | 3.0 |
| B2 | BUTYLENE GLYCOL (5) | 3.0 | 0.0 |
| C | POLYMETHYLSILSESQUIOXANE | 3.0 | 3.0 |
| | TOTAL %: | 100.0 | 100.0 |
| | TOTAL WATER PHASE %: | 75.80 | 72.60 |
| | TOTAL OIL PHASE %: | 21.30 | 24.50 |
| | RATIO (WATER PHASE/OIL PHASE): | 3.56 | 2.96 |
| | INITIAL ASPECT: | White Lotion | White Lotion |
| | 24 HR VISCOSITY (MOBILE 4, 10 MIN.): | 18.30 | 13.10 |
| | WATER RELEASING EFFECT: | FAIL | FAIL |
| | RESULTS - 10 CYCLES OF FREEZE/THAW (−20° C. to 25° C.): | Grainy (Failed) | Grainy (Failed) |

(1) ORGANIC LIQUID LIPOSOLUBLE UV FILTER
(2) ORGANIC SOLID OIL SOLUBLE UV FILTER
(3) FIRST EMULSIFIER
(4) STRUCTURING AGENT
(5) STABILITY BOOSTING POLYOL
(6) WATER SOLUBLE UV FILTER

Comparative Examples 5 and 6, as shown in Table 3, were prepared according to Examples 3 and 4 of US 2007/0274932 A1, assigned to The Procter & Gamble Company, respectively. Both Examples demonstrate the use of emulsifying silicone elastomer with an alkyl substitution and linear dimethicone crosspolymer (swelled in isododecane), while Example 6 uses an additional non-emulsifying silicone elastomer. Both Examples 5 and 6 contain less than 10% UV filters, giving low UV photoprotection benefit. Upon being exposed to the freeze/thaw stability protocol, both formulas exhibited a "grainy" and inhomogeneous appearance, indicating an inherent instability of the formulas. Upon examination under microscope, the resulting emulsions from Examples 5 and 6 exhibited large areas of detachment along the border of the emulsion in addition to plural phase separation, all indicating instability of the emulsions.

TABLE 3

Comparative Examples

| Phase | INCI US | Ex. 7 (Comparative) |
|---|---|---|
| A | DIMETHICONE (5 CST) | 7.0 |
| A | DIMETHICONE (and)15 DIMETHICONE/PEG-10/ CROSSPOLYMER (1) | 5.0 |
| B1 | WATER, PRESERVATIVE | 54.9 |
| B1 | GLYCERIN (2) | 15.0 |
| B1 | PROPANEDIOL (2) | 3.0 |
| B1 | SODIUM HYDROXIDE | 0.1 |
| B2 | TEREPHTHALYLIDENE DICAMPHOR SULFONIC ACID (50% aqueous solution) (3) | 9.0 |
| B2 | PHENYLBENZIMIDAZOLE SULFONIC ACID (3) | 3.0 |
| B2 | WATER | 7.2 |
| B2 | TRIETHANOLAMINE | 1.8 |
| B2 | SODIUM HYDROXIDE | 0.4 |
| C | POLYMETHYLSILSESQUIOXANE | 0.5 |
| | TOTAL %: | 100.0 |
| | TOTAL WATER PHASE %: | 87.50 |
| | TOTAL OIL PHASE %: | 12.00 |
| | RATIO (WATER PHASE/OIL PHASE): | 7.29 |
| | INITIAL ASPECT: | Slightly Translucent Yellow Gel-Like Cream |
| | MICROSCOPE ANALYSIS | *fine, uniform emulsion with tight edges |

TABLE 3-continued

| | | Comparative Examples |
|---|---|---|
| Phase | INCI US | Ex. 7 (Comparative) |
| | 24 HR VISCOSITY (MOBILE 4, 10 MIN.): | 23.20 |
| | WATER RELEASING EFFECT: | Pass |
| | RESULTS - 10 CYCLES OF FREEZE/THAW (−20° C. to 25° C.): | *passed - no crystallization or emulsion separation |
| | SUN PROTECTION (5 SUBJECT SCREENING - ISO METHOD): | SPF = 9 |

(1) FIRST EMULSIFIER
(2) STABILITY BOOSTING POLYOL
(3) WATER SOLUBLE UV FILTER

TABLE 4

| | | Inventive Examples | | | |
|---|---|---|---|---|---|
| Phase | INCI US | Ex. 8 (Inventive) | Ex. 9 (Inventive) | Ex. 10 (Inventive) | Ex. 11 (Inventive) |
| A | DICAPRYLYL ETHER | 0 | 2.0 | 2.0 | 2.0 |
| A | DIMETHICONE | 7.0 | 5.0 | 5.0 | 5.0 |
| A | OCTOCRYLENE (1) | 5.0 | 5.0 | 5.0 | 5.0 |
| A | ETHYLHEXYL SALICYLATE (1) | 5.0 | 5.0 | 5.0 | 5.0 |
| A | DROMETRIZOLE TRISILOXANE (2) | 0 | 3.0 | 3.0 | 3.0 |
| A | C30-45 ALKYLDIMETHYLSILYL POLYPROPYLSILSESQUIOXANE (AND) PARAFFIN | 0 | 0 | 2.0 | 2.0 |
| A | TITANIUM DIOXIDE (AND) DIMETHICONE | 0.3 | 0.3 | 0.3 | 0.3 |
| A | DIMETHICONE (and) DIMETHICONE/PEG-10/15 CROSSPOLYMER (3) | 5.0 | 7.0 | 7.0 | 7.0 |
| B | WATER, PRESERVATIVE | 33.275 | 42.875 | 40.875 | 51.700 |
| B | GLYCERIN | 15.0 | 15.0 | 15.0 | 15.0 |
| B | CAPRYLYL GLYCOL | 0.5 | 0.5 | 0.5 | 0.5 |
| B | PROPANEDIOL | 3.0 | 3.0 | 3.0 | 3.0 |
| B | TEREPHTHALYLIDENE DICAMPHOR SULFONIC ACID (4) | 9.0 | 9.0 | 9.0 | 0 |
| B | SODIUM HYDROXIDE | 0.625 | 0.025 | 0.025 | 0 |
| B | WATER | 10.0 | 0 | 0 | 0 |
| B | PHENYLBENZIMIDAZOLE SULFONIC ACID (4) | 4.0 | 0.0 | 0 | 0 |
| B | TRIETHANOLAMINE | 1.8 | 1.8 | 1.8 | 0.000 |
| C | POLYMETHYLSILSESQUIOXANE | 0.5 | 0.5 | 0.5 | 0.5 |
| | TOTAL %: | 100.00 | 100.00 | 100.00 | 100.00 |
| | FIRST EMULSIFIER %: | 1.40 | 1.96 | 1.96 | 1.96 |
| | TOTAL WATER PHASE %: | 77.20 | 72.20 | 70.20 | 70.20 |
| | TOTAL OIL PHASE %: | 22.30 | 27.30 | 29.30 | 29.30 |
| | RATIO (WATER PHASE/OIL PHASE): | 3.46 | 2.64 | 2.40 | 2.40 |
| | INITIAL ASPECT: | White Cream | White Cream | White Cream | Creamy Lotion |
| | 24 HR VISCOSITY (MOBILE 3, 10 MIN.): | 64.10 | 35.60 | 64.90 | 43.50 |
| | WATER RELEASING EFFECT: | Pass | Pass | Pass | Pass |
| | STABILITY RESULTS: | *passed 12 weeks (25 C., 37 C. & 45 C.) + 10 days at F/T | *passed 12 weeks (25 C., 37 C. & 45 C.) + 10 days at F/T | *passed 12 weeks (25 C., 37 C. & 45 C.) + 10 days at F/T | *passed 12 weeks (25 C., 37 C. & 45 C.) + 10 days at F/T |
| | VISCOSITY (MOBILE 3, 10 MIN.) AT STABILITY TEST POINTS: | wk. 4: 25 C. = 66.1, 45 C. = 68.7 wk. 8: 25 C. = 61.9, 45 C. = 58.5 wk. 12: 25 C. = 63.7, 45 C. = 66.9 | wk. 4: 25 C. = 34.6, 45 C. = 35.2 wk. 8: 25 C. = 35.7, 45 C. = 34.6 wk. 12: 25 C. = 35.5, 45 C. = 33.9 | wk. 4: 25 C. = 65.8, 45 C. = 63.5 wk. 8: 25 C. = 65.4, 45 C. = 62.9 wk. 12: 25 C. = 64.9, 45 C. = 64.3 | not measured |
| | SUN PROTECTION RESULTS: | *broad spectrum UV protection - international ISO methods 5 subject screen test results: SPF = | *broad spectrum UV protection - international ISO methods 5 subject screen test results: | *broad spectrum UV protection - international ISO methods 5 subject screen test results: | not measured |

TABLE 4-continued

Inventive Examples

| Phase | INCI US | Ex. 8 (Inventive) | Ex. 9 (Inventive) | Ex. 10 (Inventive) | Ex. 11 (Inventive) |
|---|---|---|---|---|---|
| | | 22.0/UVA-PF = 9.3 | SPF = 24.6/ UVA-PF = 8.9 | SPF = 20.4/ UVA-PF = 8.9 | |

(1) ORGANIC LIQUID LIPOSOLUBLE UV FILTER
(2) ORGANIC SOLID OIL SOLUBLE UV FILTER
(3) FIRST EMULSIFIER
(4) WATER SOLUBE UV FILTER

In making each of the examples in Tables 1-4, the following procedure is used. The ingredients of Phase A (oil phase) were placed in a main beaker and were mixed well with a s sweep blade while heating to 75-80° C. until uniform. The ingredients of Phase B (aqueous) were mixed together in a side beaker with a stir bar or propeller mixer and were heated to about 75-80° C. until all solids were dissolved. The mixture of aqueous phase ingredients (Phase B) was slowly added to the mixed ingredients of Phase A (oil phase) using sweep mixing over a period of about 10 minutes for about a 1 kg batch. As the viscosity of the mixture increased, the stirring speed was increased. As the aqueous phase is mixed into the oil phase, a water-in-oil emulsion was formed. After cooling the batch to about 30° C. while continuing to mix with a sweep blade, the powder of phase C was added to the batch and mixed with sweep mixing into the water-in-oil emulsion until homogeneous.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A sunscreen composition comprising:
   an aqueous phase containing at least one water-soluble ingredient; and
   an oil phase comprising:
      a first emulsifier comprising an emulsifying crosslinked siloxane elastomer at a concentration, by weight, of from about 5%, based upon weight of the composition;
      dimethicone at a concentration, by weight, of from about 1% to about 25%, based on the total weight of the composition; and
      at least one liquid organic liposoluble UV filter at a concentration from 10% to greater than 10%, by weight, based on the total weight of the composition;
   wherein a phase ratio of the aqueous phase to the oil phase is about 1.0 to about 12.0, the sunscreen composition is stable and does not demonstrate crystallization or emulsion separation after 10 cycles of freeze thaw from −25° C. to 25° C., has a sun protection factor (SPF) of greater than or equal to 15 and converts from an emulsion to a plurality of droplets upon application of shear when applied to a keratinous substrate; wherein a water-releasing effect is achieved by placing the sunscreen composition on the keratinous substrate, then gently and repeatedly rubbing with fingers in a circling motion resulting in the formation of a plurality of distinct spherical water droplets or a continuous streak of water droplets.

2. The sunscreen composition according to claim 1, further comprising in the oil phase a powder present at a concentration, by weight, of from about 0.1% to about 10%, based upon weight of the composition.

3. The sunscreen composition according to claim 2, wherein the first emulsifier is selected from the group consisting of substituted or unsubstituted dimethicone/copolyol crosspolymer; dimethicone/PEG-10/15 crosspolymers; substituted or unsubstituted dimethicone/polyglyceryl crosspolymer; dimethicone/polyglycerin-3 crosspolymer; PEG-15/lauryl polydimethylsiloxyethyl dimethicone crosspolymer; and combinations thereof.

4. The sunscreen composition according to claim 3, wherein the first emulsifier is dimethicone/PEG-10/15 crosspolymer.

5. The sunscreen composition according to claim 4, wherein the first emulsifier is dimethicone/PEG-10/15 crosspolymer and PEG-15/lauryl polydimethylsiloxyethyl dimethicone crosspolymer.

6. The sunscreen composition according to claim 4, wherein the composition further includes a second emulsifier at a concentration, by weight, that does not exceed 1%, based upon the weight of the composition.

7. The sunscreen composition according to claim 6, wherein the second emulsifier is present at a concentration, by weight, of from about 0.01% to about 1.00%, based upon weight of the composition.

8. The composition of claim 1, wherein the liquid organic liposoluble UV filter is selected from the group consisting of menthyl anthranilate; cinnamic derivatives selected from the group consisting of ethylhexyl methoxycinnamate; salicylic derivatives selected from the group consisting of homosalate, ethylhexyl salicylate; β,β-diphenylacrylate derivatives selected from the group consisting of octocrylene; p-aminobenzoic acid (PABA) derivatives selected from the group consisting of ethylhexyl dimethyl PABA; polymer sunscreens and silicone sunscreens; dimers derived from α-alkylstyrene; 4,4-diarylbutadienes, and combinations thereof.

9. The composition of claim 8, wherein the liquid organic liposoluble UV filter is selected from the group consisting of homosalate, ethylhexyl salicylate, octocrylene, ethylhexyl methoxycinnamate, ethylhexyl dimethyl PABA, isoamyl p-methoxycinnamate, and combinations thereof.

10. The composition of claim 8, wherein the liquid organic liposoluble UV filter is selected from the group consisting of octocrylene, ethylhexyl salicylate, homosalate, and combinations thereof.

11. The sunscreen composition according to claim 1, wherein the composition further includes a solid organic liposoluble UV filter present at a concentration, by weight, of at least 1%, based upon weight of the composition.

12. The sunscreen composition according to claim 1, wherein the composition is substantially devoid of solid organic liposoluble UV filters.

13. The sunscreen composition according to claim 1, wherein the aqueous phase further includes a water-soluble UV filter.

14. The sunscreen composition according to claim 1, wherein the oil phase further includes a structuring agent.

15. The composition of claim 1, wherein the ratio of the aqueous phase to the oil phase is from about 1.0 to about 5.0.

16. The composition of claim 1, wherein the ratio of the aqueous phase to the oil phase is from about 1.0 to about 3.5.

17. The sunscreen composition of claim 1, wherein the at least one water soluble ingredient of the aqueous phase is at least one polyol at a concentration, by weight, of from about 5% to about 30%, based upon weight of the composition.

18. A sunscreen composition comprising:
an aqueous phase containing at least one water-soluble ingredient; and
an oil phase comprising:
a first emulsifier, the first emulsifier being dimethicone and dimethicone/PEG-10/15 crosspolymers at a concentration, by weight, of from about 5%, based upon weight of the composition;
dimethicone at a concentration, by weight, of from about 4% to about 15%, based on the total weight of the composition; and
at least one liquid organic liposoluble UV filter at a concentration from greater than 10% by weight, based on the total weight of the composition;
wherein a phase ratio of the aqueous phase to the oil phase is about 1.0 to about 5.0, the sunscreen composition is stable and does not demonstrate crystallization or emulsion separation after 10 cycles of freeze thaw from −25° C. to 25° C., has a sun protection factor (SPF) of from about 15 to about 30 and converts from an emulsion to a plurality of droplets upon application of shear when applied to a keratinous substrate; wherein a water-releasing effect is achieved by placing the sunscreen composition on the keratinous substrate, then gently and repeatedly rubbing with fingers in a circling motion resulting in the formation of a plurality of distinct spherical water droplets or a continuous streak of water droplets.

19. A sunscreen composition comprising:
an aqueous phase containing at least one water-soluble ingredient; and
an oil phase consisting of:
an emulsifying crosslinked silicone emulsifier at a concentration, by weight, of from about 0.1% to about 20%, based upon weight of the composition;
an optional second emulsifier, when present, at a concentration, by weight, of less than 1%, based upon the weight of the composition;
dimethicone at a concentration, by weight, of from about 4% to about 15%, based on the total weight of the composition;
an optional emollient;
an optional structuring agent, when present, at a concentration, by weight, of from about 0.1% to about 5%, based upon the weight of the composition;
an optional powder, when present, at a concentration, by weight, of from about 0.1% to about 10%, based upon weight of the composition;
at least one liquid organic liposoluble UV filter at a concentration from greater than 10%, by weight, based on the total weight of the composition,
an optional solid organic liposoluble UV filter, when present, at a concentration of at least 1%, by weight, based on the total weight of the composition;
wherein a phase ratio of the aqueous phase to the oil phase is about 1.0 to about 5.0, the sunscreen composition is stable and does not demonstrate crystallization or emulsion separation after 10 cycles of freeze thaw from −25° C. to 25° C., has a sun protection factor (SPF) of greater than or equal to 15 and converts from an emulsion to a plurality of droplets upon application of shear when applied to a keratinous substrate; wherein a water-releasing effect is achieved by placing the sunscreen composition on the keratinous substrate, then gently and repeatedly rubbing with fingers in a circling motion resulting in the formation of a plurality of distinct spherical water droplets or a continuous streak of water droplets.

20. A process for inhibiting UV rays from contacting a surface comprising the steps of:
applying the composition of claim 1 onto a keratinous substrate; and
applying shear onto the composition, thereby transforming the composition into a plurality of droplets.

* * * * *